US009575012B2

(12) United States Patent
Lin et al.

(10) Patent No.: US 9,575,012 B2
(45) Date of Patent: Feb. 21, 2017

(54) AUTOMATED WAFER INSPECTION

(71) Applicant: Taiwan Semiconductor Manufacturing Company Limited, Hsin-Chu (TW)

(72) Inventors: Hu-Wei Lin, Hsinchu (TW); Hsiao-Yu Chen, Taichung District (TW); Jr-Wei Ye, Erlin Township (TW); Hong-Hsing Chou, Jhubei (TW); Chih-Hsien Hsu, Hsinchu (TW); Tsung-Cheng Huang, Jhubei (TW); Hua-Kuang Teng, Qionglin Township (TW); Hsieh Chi-Jen, Toufen Township (TW); Chun-Chih Chen, Zhongli (TW)

(73) Assignee: Taiwan Semiconductor Manufacturing Company Limited, Hsin-Chu (TW)

( * ) Notice: Subject to any disclaimer, the term of this patent is extended or adjusted under 35 U.S.C. 154(b) by 571 days.

(21) Appl. No.: 14/039,639

(22) Filed: Sep. 27, 2013

(65) Prior Publication Data

US 2014/0267692 A1 Sep. 18, 2014

Related U.S. Application Data

(60) Provisional application No. 61/800,549, filed on Mar. 15, 2013.

(51) Int. Cl.
*G01N 21/95* (2006.01)

(52) U.S. Cl.
CPC ................. *G01N 21/9501* (2013.01)

(58) Field of Classification Search
CPC ... H01L 21/00; G01N 21/9501; G01N 21/956; G01N 21/21; G01N 21/95607; G01N 2021/8858

See application file for complete search history.

(56) References Cited

U.S. PATENT DOCUMENTS

| 2002/0186368 A1* | 12/2002 | Rosengaus | ......... G01N 21/9501 356/237.2 |
| 2003/0054657 A1* | 3/2003 | Kim | .................. H01J 37/32935 438/710 |
| 2005/0146716 A1* | 7/2005 | Dixon | .................. G01N 21/278 356/237.4 |
| 2013/0112223 A1* | 5/2013 | Nakaharada | ...... H01L 21/67046 134/18 |

\* cited by examiner

*Primary Examiner* — Obafemi Sosanya
(74) *Attorney, Agent, or Firm* — Cooper Legal Group, LLC (57) ABSTRACT

In semiconductor fabrication processes, one or more wafers are often exposed to processes such as chemical vapor deposition to form semiconductor components thereupon. Often, some of the wafers exhibit flaws due to contamination or processing errors occurring before, during, or after component formation. Inspection of the wafers is often performed by direct visual inspection of humans, which is prone to errors due to flaws that are too small to view directly; to particles naturally arising in the human eye; and to fatigue caused by inspection of large numbers of wafers. Presented herein are inspection techniques involving positioning the wafer in a dark chamber exposing the surface of the wafer to a light source at a first angle, and capturing with a camera an image of the light source reflected from the surface of the wafer at a second angle. Wafers identified as exhibiting flaws are removed from the wafer set.

20 Claims, 7 Drawing Sheets

AUTOMATED WAFER INSPECTION

BACKGROUND

The present disclosure is related to semiconductor fabrication techniques involving an inspection of a wafer for flaws, such as contamination from dust particles, malformed wafers, and errors in the deposition process.

SUMMARY

This Summary is provided to introduce a selection of concepts in a simplified form that are further described below in the detailed description. This summary is not intended to be an extensive overview of the claimed subject matter, identify key factors or essential features of the claimed subject matter, nor is it intended to be used to limit the scope of the claimed subject matter.

In many such semiconductor fabrication techniques, a wafer provided as a substrate for the formation of semiconductor components exhibits various flaws, which arise before, during, or after the fabrication process. Wafer inspection is often performed by visual inspection, where a human visually examines the surface of the wafer to spot visible defects for removal from the fabrication process in order to reduce errors and the formation of nonfunctional components. However, direct human visual inspection are undesirably inaccurate, and human fatigue produces errors in the inspection process. For example, many flaws are too small to be identified accurately by the human eye. The complication of patterns on wafers, shadows caused by particles on wafers, reflections and refractions of light, etc also make it more difficult to inspect the wafers by direct visual inspections.

The techniques presented herein involve wafer inspection by capturing an image of the wafer. As one example, a wafer is positioned in a dark chamber that reduces other sources of light, and while a light source illuminates the surface of the wafer, an image of the light reflected from the surface of the wafer is captured by a camera. The resulting image is inspected by a human and/or an image evaluation technique to identify flaws in the wafer.

To the accomplishment of the foregoing and related ends, the following description and annexed drawings set forth certain illustrative aspects and implementations. These are indicative of but a few of the various ways of embodying one or more aspects of the presented techniques. Other aspects, advantages, and novel features of the disclosure will become apparent from the following detailed description when considered in conjunction with the annexed drawings.

DESCRIPTION OF THE DRAWINGS

Aspects of the disclosure are understood from the following detailed description when read with the accompanying drawings. It will be appreciated that elements and structures of the drawings are not necessarily be drawn to scale. Accordingly, the dimensions of the various features is arbitrarily increased and reduced for clarity of discussion.

DETAILED DESCRIPTION

Embodiments or examples, illustrated in the drawings, are disclosed below using specific language. It will nevertheless be understood that the embodiments or examples are not intended to be limiting. Any alterations and modifications in the disclosed embodiments, and any further applications of the principles disclosed in this document are contemplated as would normally occur to one of ordinary skill in the pertinent art.

In semiconductor fabrication techniques, a wafer is positioned in a chemical vapor deposition chamber, and particles of a dopant are implanted into regions of the surface of the wafer to induce electronic conductivity. The surface of the wafer is exposed to a variety of deposition processes to form a series of layers thereupon. The wafer is further processed to remove layers from some regions of the surface of the wafer, and other layers are formed thereupon, resulting in the precise manufacturing of semiconductor components, such as controllably conductive gate structures.

Because these processes are often precisely performed on a very small scale, the fabrication process is sensitive to flaws, such as dust and other contaminants, that alter the physical, chemical, and electronic properties of the semiconductor components formed on the wafer, resulting in a malfunction. Processing such wafers in a controlled environment, such as a clean room, is capable of reducing but not completely eliminating contamination. Other flaws are caused by malformation of the substrate of the provided wafers and errors in the fabrication process, such as machine errors and mishandling by humans. As a result, a subset of wafers processed in this manner result in inefficiencies such as a loss of materials, and incorrect or unpredictable operation in a particular percentage of the resulting semiconductor devices.

Figure 1:
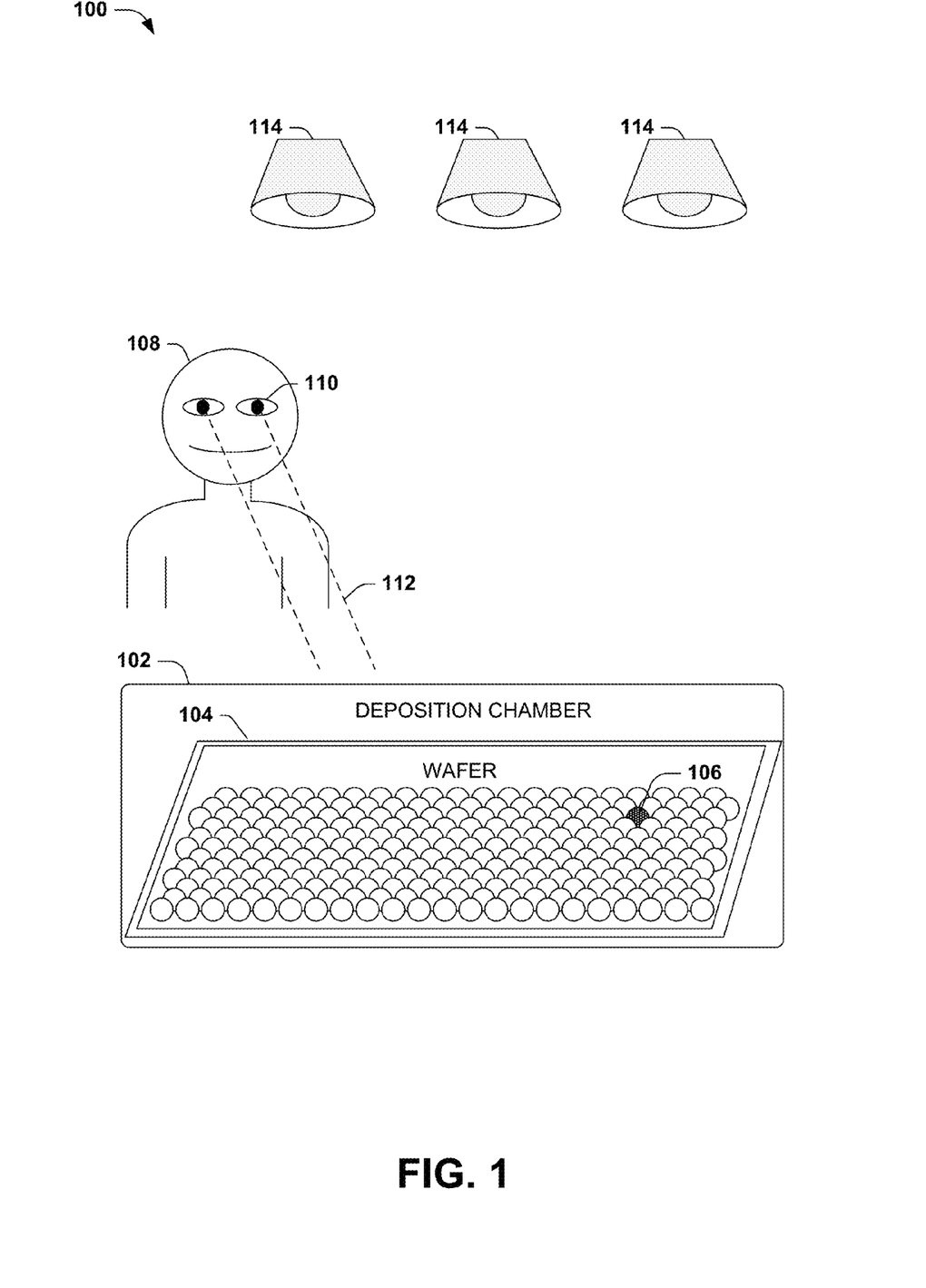
FIG. 1 is an illustration of a first inspection technique for identifying flaws in wafers.

FIG. 1 depicts an exemplary scenario 100 featuring a first technique for reducing the inefficiency presented by flawed wafers 104. In this exemplary scenario 100, before, during, or after the processing of a wafer 104 (such as in a deposition chamber 102), an individual 108 performs a visual inspection 112 to identify flaws 106 that are visible in the surface of the wafer 104. Such flaws often appear as discontinuities or discoloration in a portion of the wafer 104, and are often visible to the human eye 110. The visual inspection 112 by the individual 108 results in the identification of a significant number of wafers 104 having flaws 106, which are removed from the semiconductor fabrication process. However, visual inspection 112 by an individual 108 occasionally misses some flaws 106 that are too small to visualize with the human eye 112, and occasionally misidentifies non-flawed wafers 104 as flawed, for example, the complication of patterns on wafers, shadows caused by particles on wafers, reflections and refractions of light that are mistaken for flaws 106. Additional errors result from glare caused by the light sources 114 present in the environment of the individual 108 that obscures some flaws 106, and fatigue caused by the visual examination 110 of a large number of wafers 104 in a period such as a day.

Figure 2:
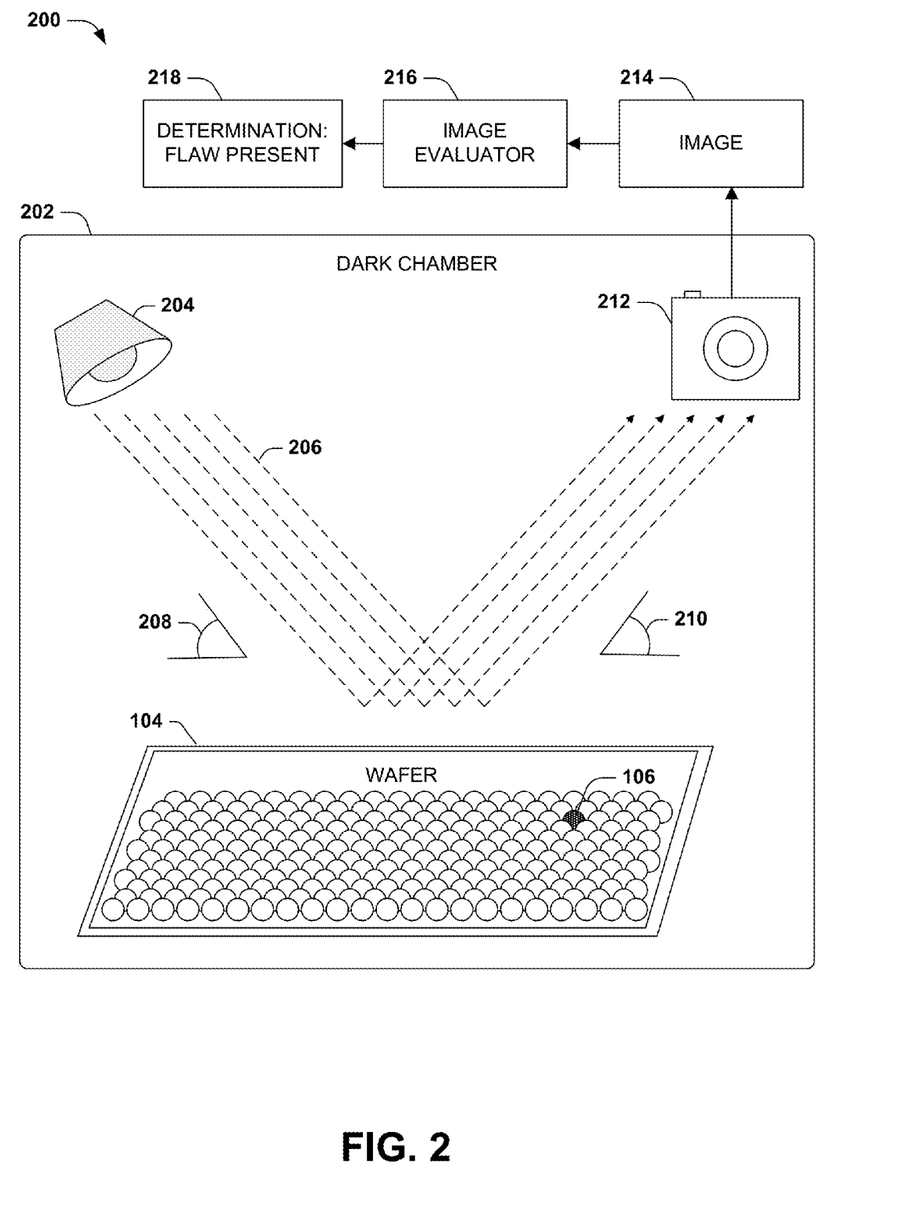
FIG. 2 is an illustration of a second inspection technique for identifying flaws in wafers in accordance with the techniques presented herein.

FIG. 2 presents an illustration of an exemplary scenario 200 featuring a second technique for inspecting wafers 104 for flaws 106 as part of the semiconductor fabrication process. In this exemplary scenario 200, the wafer 104 is positioned in a dark chamber 202 that excludes light from light sources 118 outside of the dark chamber 202. The surface of the wafer 104 is illuminated by a light source 204 oriented toward the wafer 104 at a first angle 208, such as a 45° angle. Light 206 emitted from the light source 204 reflects from the surface of the wafer 104 at a second angle 210, and is captured with a camera 212, resulting in an image 214 of the surface of the wafer 104. The image 214 is evaluated with an image evaluator 216, such as a presentation of the image 214 to an individual 108 for visual inspection 112 of the image 214, or a machine vision or other image evaluation technique, to identify at least one flaw 106 in the wafer 104. If at least one flaw 106 is identified in the image 214 of the surface of the wafer 104, the wafer 104 is removed from the semiconductor fabrication process; and if no flaws 106 are found in the image 214 of the surface of the wafer 104, the wafer 104 continues through the semiconductor fabrication process. In this manner, the exemplary scenario 200 presents an inspection that identifies flaws 106 in wafers 104 according to the techniques presented herein.

Figure 3:
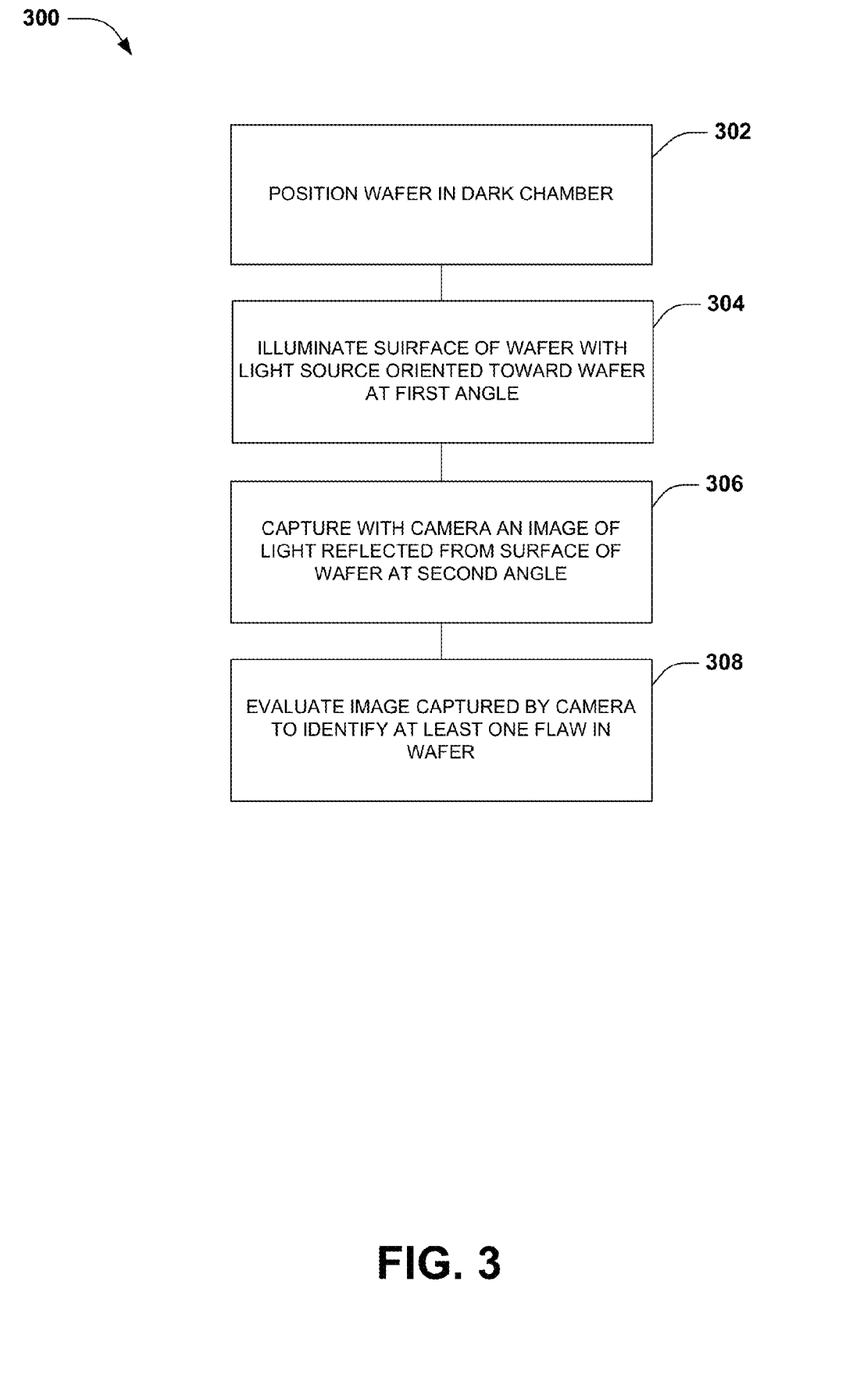
FIG. 3 is a flow diagram of a method of identifying flaws in a wafer.

FIG. 3 is a flow diagram of an exemplary method 300 of inspecting a wafer 104. The exemplary method 300 involves positioning 302 the wafer 104 in a dark chamber 202. The exemplary method 300 also involves illuminating 304 the surface of the wafer 104 with a light source 204 oriented toward the wafer 104 at a first angle 208. The exemplary method 300 also involves capturing 306, with a camera 212, an image 214 of the light 206 reflected from the surface of the wafer 104 at a second angle 210. The exemplary method 300 also involves evaluating 308 the image 214 captured by the camera 212 to identify at least one flaw 106 in the wafer 104. In this manner, the exemplary method 300 achieves the inspection of the wafer 104 in accordance with the techniques presented herein.

Figure 4:
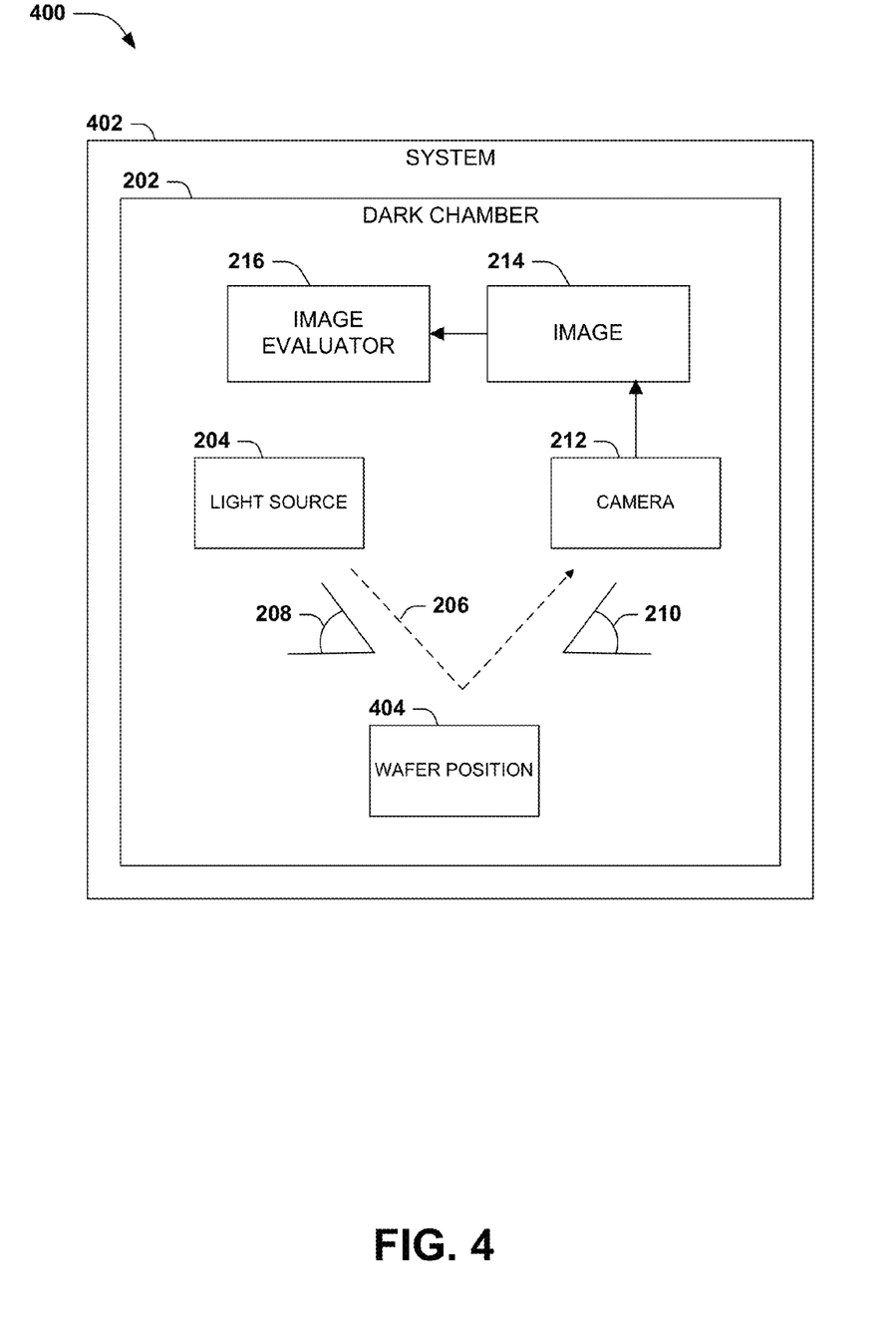
FIG. 4 is a component block diagram of a system configured to identify flaws in wafers.

FIG. 4 is a component block diagram 400 of an exemplary system 402 for inspecting wafers 104. The exemplary system 402 includes a dark chamber 202 having a chamber interior including a wafer position 404. The exemplary system 402 also includes a light source 204 oriented to emit light 206 at a first angle 208 toward a surface of a wafer 104 positioned at the wafer position 404. The exemplary system 402 also includes a camera 212 oriented toward the wafer position 404 and configured to capture an image 214 of the light 206 emitted by the light source 204 and reflected at a second angle 210 from the surface of the wafer 104. The exemplary system 402 also includes an image evaluator 216 configured to evaluate the image 214 of the surface of the wafer 104 to identify at least one flaw 106 in the wafer 104. The components of the exemplary system 402 thus interoperate to achieve the inspection of wafers 104 for flaws 106 as part of the semiconductor fabrication process.

Figure 5:
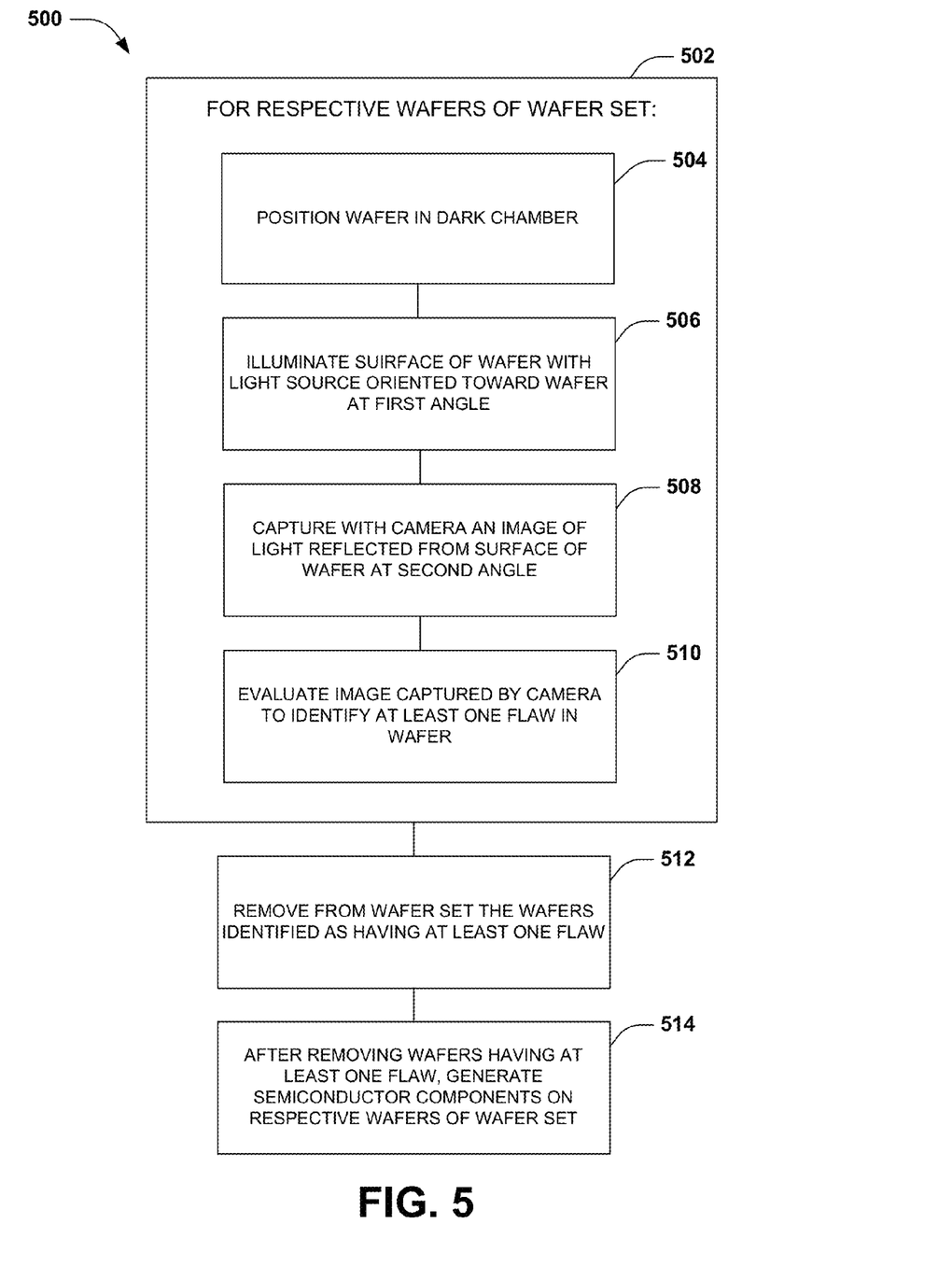
FIG. 5 is a flow diagram of a method of generating semiconductor components on a wafer set comprising at least one wafer.

FIG. 5 is an illustration of an exemplary method 500 of generating semiconductor components on a wafer set comprising at least one wafer 104. The exemplary method 500 involves, for respective 502 wafers 104 of the wafer set, positioning 504 the wafer 104 in a dark chamber 202; illuminating a surface of the wafer 104 with a light source 204 oriented toward the wafer 104 at a first angle 208; capturing 506, with a camera 212, an image 214 of light reflected from the surface of the wafer 104 at a second angle 210; and evaluating 510 the image 214 of the surface of the wafer 104 to identify at least one flaw 106 in the wafer 104. The exemplary method 500 also involves removing 512 from the wafer set the wafers 104 identified as having at least one flaw 106. The exemplary method 500 also involves, after removing 512 the wafers 104 identified as having at least one flaw 106, generating 514 at least one semiconductor components on respective wafers 104 of the wafer set. In this manner, the exemplary method 500 achieves the generation of semiconductor components on the wafers 104 of the wafer set in accordance with the techniques presented herein.

Various embodiment of the techniques presented herein are capable of including variations in one or more aspects, where such variations are capable of conferring advantages and/or alleviating disadvantages with respect to other variations of such aspects.

As a first aspect, several different types of light sources 204 are usable in order to expose the wafer 104 to different types of light 206. In a first embodiment, the light source 204 is polarity filtered, such that the light 206 reflected form the wafer 104 and captured by the camera 212 in the image 214 includes a first polarity of the light 206 and to exclude a second polarity of the light 206. In a second embodiment, the light source 204 is configured to emit light 206 within a wavelength range, such as a portion of a visible wavelength range representing the visible spectrum; an infrared wavelength range; and an ultraviolet wavelength range. Some such wavelengths promote the accurate identification of flaws 106 in the surface of the wafer 104. In a third embodiment, the shape, size, focus, and/or intensity of the light 206 emitted by the light source 204 are selected. In one such embodiment, a planar light source is utilized to expose the wafer 104 to a plane of light 206. In a fourth embodiment, the first angle 208 at which the light source 204 is oriented to emit light 206 toward the wafer 104 and/or the second angle 210 at which the light 206 is reflected from the surface of the wafer 104 and captured by the camera 212 are selected to promote the capturing and evaluation of images 214 that result in the identification of flaws 106 in the wafer 104. In one such embodiment, the first angle 208 approximately equals the second angle 210, such as 45° angles.

As a second aspect, various properties of the techniques presented herein (such as the exemplary system 202 in the exemplary scenario 200 of FIG. 2) are altered during the capturing of one or more images 214. In a first embodiment, while capturing with the camera 212 the image 214 of the surface of the wafer 104, the first angle 208 of the light source 204 oriented toward the wafer 104 is altered. This alteration is achievable by altering a position of the wafer 104 (such as rotating, tilting, shifting, and/or displacing the wafer 104) and/or the light source 204 (such as rotating, tilting, shifting, and/or displacing the light source 204). In a second embodiment, while capturing with the camera 212 the image 214 of the surface of the wafer 104, the second angle 210 of the camera 212 oriented toward the wafer 104 is adjusted. This alteration is achievable by altering a position of the wafer 104 (such as rotating, tilting, shifting, and/or displacing the wafer 104) and/or the camera 212 (such as rotating, tilting, shifting, and/or displacing the camera). In a third embodiment, while capturing with the camera 212 the image 214 of the surface of the wafer 104, the position of the wafer 104 with respect to the light source 204, the position of the wafer 104 with respect to the camera 212, and/or the position of the light source 204 with respect to the camera 212 are altered, such as by rotating or displacing one such component with respect to another such component. In a fourth embodiment, while capturing with the camera 212 the image 214 of the surface of the wafer 104, a wavelength range of the light 206 emitted by the light source 204 is altered, such as shifting from a first portion of the visible spectrum to a second portion of the visible spectrum. In a fifth embodiment, while capturing with the camera 212 the image 214 of the surface of the wafer 104, the polarity filtering of the light 206 emitted by the light source 204 is altered, such as by rotating a circular polarity filter to select a variety of polarity ranges of the light 206.

As a third aspect, various evaluation techniques are utilized to evaluate the image 214 of the surface of the wafer 104 to identify flaws 106. In a first embodiment, the image 214 is evaluated by presenting the image 214 to an individual 108, and receiving from the individual 108 an evaluation indicating at least one flaw 106 in the wafer 104. Such inspection techniques are capable of presenting various advantages with respect to the direct visual inspection 112 depicted in the exemplary scenario 100 of FIG. 1. For example, higher accuracy in the visual inspection 112 of images 214 by an individual is achievable by altering the contrast of the image 214 to accentuate visible flaws 106; by presenting the image 214 at a high zoom level to facilitate the visibility of flaws 106 that are difficult to detect through direct visual observation 112; and by reducing glare from the light sources 114 within the environment that obscure flaws 106 on the surface of the wafer 104. In a second embodiment, the image 214 is evaluated with an image evaluator 216 that is configured to identify flaws 106 in images 214 of wafers 104, such as a machine vision or image processing algorithm, and receiving from the image evaluator 216 an evaluation indicating at least one flaw 106 in the wafer 104. In a third embodiment, the image evaluator 216 is configured to identify a flaw count of the at least one flaw 106 in the wafer 104, and compare the flaw count with a flaw count threshold, thereby determining the extent or significance of the flaws 106 in the wafer 104 and/or a comparison of the degree of contamination with a fault tolerance of the fabrication process. In a fourth embodiment, the image evaluator 216 is further configured to measure the at least one flaw 106, such as the diameter, length, and/or depth of the flaw 106.

Figure 6:
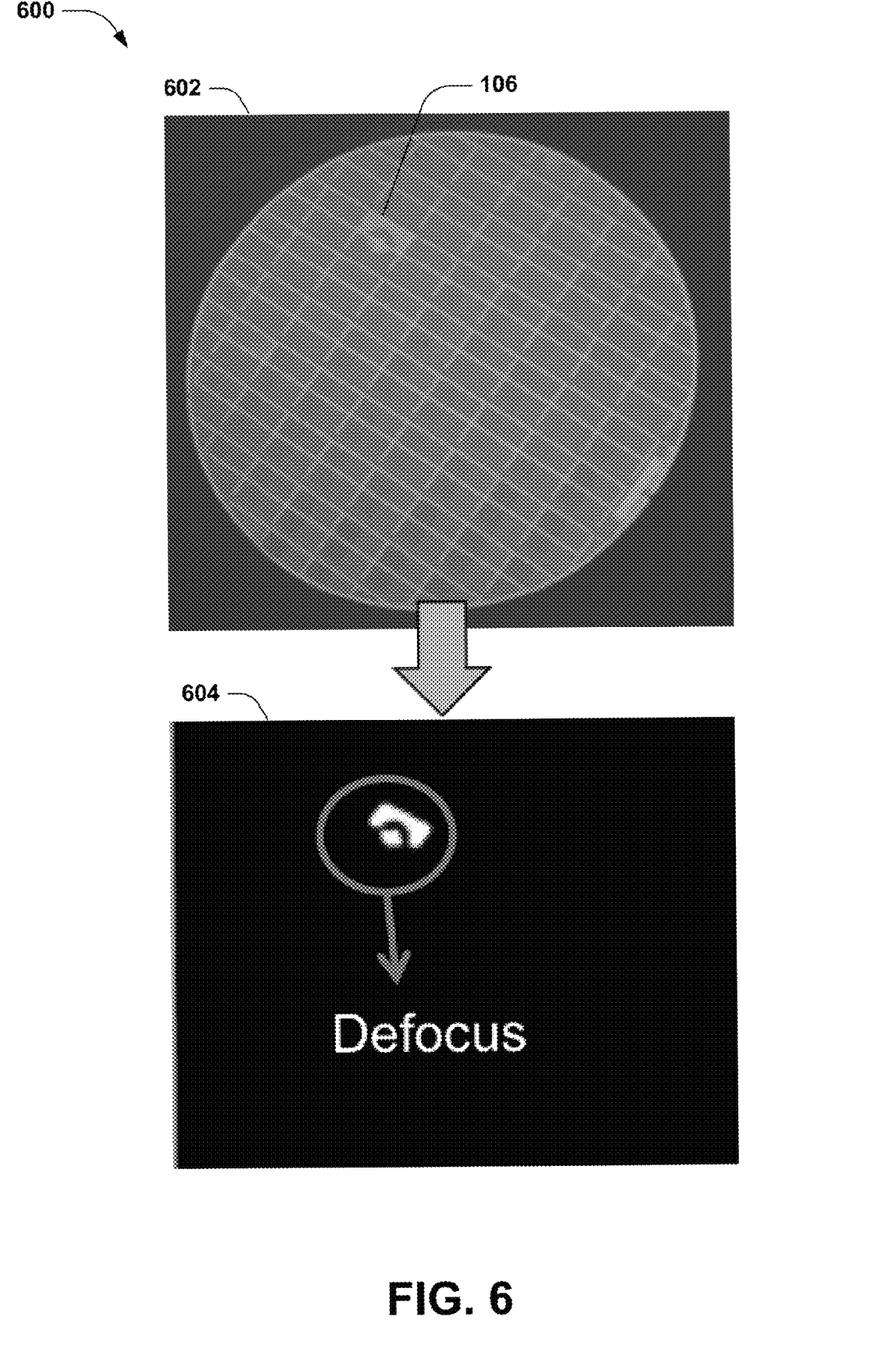
FIG. 6 is a comparison of a pair of images of a wafer exhibiting a flaw.

FIG. 6 presents a comparison 600 of a pair of images 214 of a wafer 104 exhibiting a flaw 106 and captured according to the techniques presented herein. In a first image 602, the wafer 104 is depicted with a flaw 106 visible as a discontinuity, but the comparatively low contrast of the first image 602 reduces the identification of the flaw 106 during visual inspection 114 or an automated algorithm. After a process enhancing the image quality of first image 602 into a second image 604, the contrast is significantly increased and the defocused flaw 106 is more easily and reliably identifiable on the second image 604.

As a fourth aspect, in some embodiments, a first image 214 of a wafer 104 is captured by the camera 212. In a first embodiment, the camera 212 captures a first image 214 that is evaluated with the image evaluator 216 to identify at least one flaw 106 in the wafer 104. In the image evaluator 216, the images 214 can be directly compared with a reference image of an unflawed wafer to determine whether flaws exist in the wafer 104. In another embodiment, the images 214 are enhanced into processed images and compared with the reference image to identify if flaws exist in the wafer 104.

Figure 7:
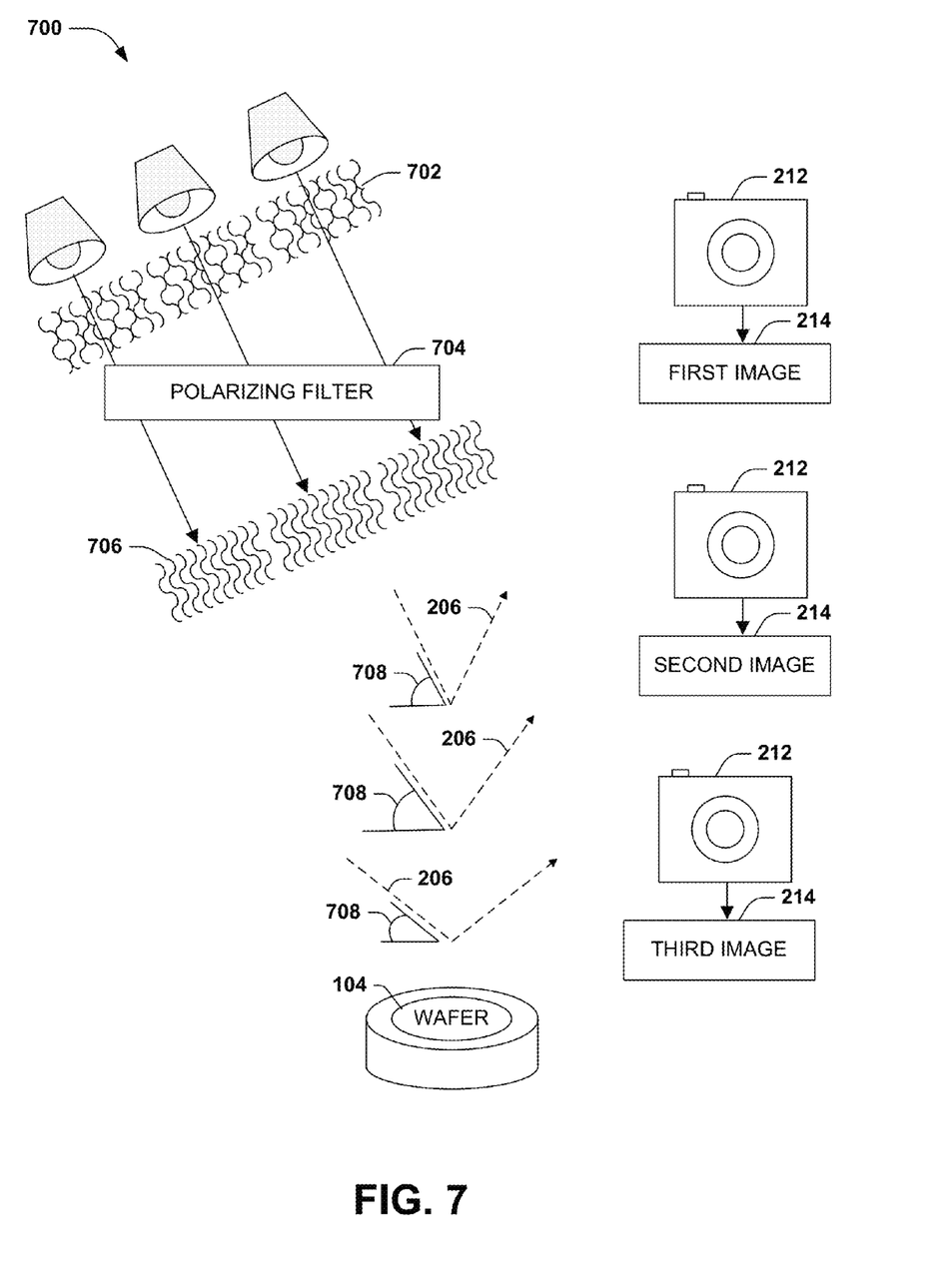
FIG. 7 is an illustration of a third inspection technique for identifying flaws in wafers in accordance with the techniques presented herein.

FIG. 7 presents an illustration of an exemplary scenario 600 featuring several variations of the techniques presented herein. In this exemplary scenario 700, a set of light sources 204 is oriented toward a wafer 104 and powered to emit light 206. However, the light 206 is initially unpolarized 702, and a polarizing filter 704 positioned between the light sources 204 and the wafer 104 results in a filtering out of undesired polarities, and the emission of polarized light 706 toward the wafer 104. In some embodiments, before initiating the imaging, the wafer 104 is rotated 708 to a specific orientation. In some embodiments, the camera 212 captures a series of images 214 depicting the wafer 104 with polarized light with different incident angles 708. In various embodiments, the incident angles 708 varies with respect to a vertical axis of the wafer 104, such as by altering the height of the camera 212 with respect to the wafer 104, or a horizontal axis of the wafer 104, such as by rotating the camera 212 around the wafer 104. These images 214 are evaluated individually and/or by comparison to identify flaws 106 present in the wafer 104. Many such embodiments and variation of various aspects thereof are compatible with the techniques presented herein.

In accordance with the techniques presented herein, a first embodiment involves positioning the wafer in a dark chamber; orienting a light source toward the wafer within the dark chamber; capturing light reflected at an angle from the surface of the wafer with a camera; and evaluating the image to detect flaws in the wafer.

In accordance with the techniques presented herein, a second embodiment involves a system including a dark chamber containing a light source oriented toward the wafer; a camera oriented to capture images of the light from the light source reflected at an angle from the surface of the wafer; and an evaluation of the images to detect flaws in the wafer.

In accordance with the techniques presented herein, a third embodiment involves the processing of a wafer set by positioning each wafer in a dark chamber; exposing the wafer to light from a light source; and evaluating an image of the light reflected from the surface of the wafer and captured by a camera to detect flaws in the wafer. The wafers that result in images depicting flaws are removed from the wafer set, and the remaining wafers of the wafer set are processed to form semiconductor components.

Although the subject matter has been described in language specific to structural features and/or methodological acts, it is to be understood that the subject matter of the appended claims is not necessarily limited to the specific features or acts described above. Rather, the specific features and acts described above are disclosed as example forms of implementing the claims.

Various operations of embodiments are provided herein. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

It will be appreciated that layers, features, elements, etc. depicted herein are illustrated with particular dimensions relative to one another, such as structural dimensions and/or orientations, for example, for purposes of simplicity and ease of understanding and that actual dimensions of the same differ substantially from that illustrated herein, in some embodiments. Additionally, a variety of techniques exist for forming the layers, features, elements, etc. mentioned herein, such as implanting techniques, doping techniques, spin-on techniques, sputtering techniques such as magnetron or ion beam sputtering, growth techniques, such as thermal growth and/or deposition techniques such as chemical vapor deposition (CVD), for example.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used in either the detailed description or the claims, such terms are intended to be inclusive in a manner similar to the term "comprising".

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims.

What is claimed is:

1. A method, comprising:
   positioning a wafer in a dark chamber;
   illuminating a surface of the wafer with a light source oriented toward the wafer at a first angle;
   capturing with a camera an image of light reflected from the surface of the wafer at a second angle;
   evaluating the image captured by the camera, comprising:
     identifying at least one flaw in the wafer using the image; and
     comparing a flaw count, corresponding to a number of flaws identified in the wafer using the image, to a flaw count threshold;
   performing a first action when the flaw count is less than the flaw count threshold; and
   performing a second action different than the first action when the flaw count is more than the flaw count threshold.

2. The method of claim 1, the first angle approximately equaling the second angle.

3. The method of claim 1, further comprising:
   while capturing with the camera the image of the surface of the wafer, altering the first angle of the light source oriented toward the wafer.

4. The method of claim 1, further comprising:
   while capturing with the camera the image of the surface of the wafer, altering the second angle of the camera oriented toward the wafer.

5. The method of claim 1:
   the light source configured to emit light within a wavelength range; and
   the camera configured to capture the image of the surface of the wafer within at least a portion of the wavelength range.

6. The method of claim 5, the wavelength range selected from a wavelength range set comprising:
   a portion of a visible wavelength range;
   an infrared wavelength range; or
   an ultraviolet wavelength range.

7. The method of claim 5, further comprising:
   while capturing with the camera the image of the surface of the wafer, altering the wavelength range of the image captured by the camera.

8. The method of claim 1, further comprising:
   while illuminating the surface of the wafer with the light source, polarity filtering the light emitted by the light source to include a first polarity of the light and to exclude a second polarity of the light.

9. The method of claim 8, further comprising:
   while capturing with the camera the image of the surface of the wafer, altering an incident angle of the light with respect to the wafer.

10. The method of claim 1, further comprising:
    while capturing with the camera the image of the surface of the wafer, altering a position of the wafer relative to the light source.

11. The method of claim 1, further comprising:
    while capturing with the camera the image of the surface of the wafer, altering a position of the wafer relative to a position of the camera.

12. The method of claim 1, further comprising:
    while capturing with the camera the image of the surface of the wafer, altering a position of the light source relative to the camera.

13. The method of claim 1, evaluating the image further comprising:
    presenting the image to an individual; and
    receiving from the individual an evaluation indicating the at least one flaw in the wafer.

14. The method of claim 1, evaluating the image further comprising:
    programmatically evaluating the image with an image evaluator configured to identify flaws in images of wafers; and
    receiving from the image evaluator an evaluation indicating the at least one flaw in the wafer.

15. The method of claim 1, evaluating the image further comprising:
    measuring at least one of a diameter, a length, or a depth of the at least one flaw using the image.

16. The method of claim 1, further comprising:
    tilting the wafer relative to the camera while capturing with the camera the image of the surface of the wafer.

17. The method of claim 1, further comprising:
    at a first time point, capturing with the camera a first image of the wafer;
    evaluating the first image captured by the camera to identify at least one flaw in the wafer at the first time point;
    at a second time point that is after the first time point, capturing with the camera a second image of the wafer; and
    evaluating the second image to identify at least one flaw in the wafer at the second time point.

18. The method of claim 1, identifying the at least one flaw further comprising:
    comparing the image of the wafer with a reference image of an unflawed wafer to identify the at least one flaw.

19. A system, comprising:
    a dark chamber having a chamber interior including a wafer position;
    a light source oriented to emit light toward a surface of a wafer positioned at the wafer position at a first angle;
    a camera oriented toward the wafer position and configured to capture an image of the light emitted by the light source and reflected at a second angle from the surface of the wafer; and
    an image evaluator configured to evaluate the image of the surface of the wafer by:
      identifying at least one flaw in the wafer using the image; and comparing a flaw count, corresponding to a number of flaws identified in the wafer using the image, to a flaw count threshold, wherein:
- the system is configured to perform a first action when the flaw count is less than the flaw count threshold; and
- the system is configured to perform a second action different than the first action when the flaw count is more than the flaw count threshold.

20. A method, comprising:

for respective wafers of a wafer set:
- positioning the wafer in a dark chamber;
- illuminating a surface of the wafer with a light source oriented toward the wafer at a first angle;
- capturing with a camera an image of light reflected from the surface of the wafer while altering a position of the light source relative to the camera; and
- evaluating the image of the surface of the wafer to identify at least one flaw in the wafer;

removing from the wafer set the wafers identified as having at least one flaw; and after removing the wafers identified as having at least one flaw, generating at least one semiconductor component on respective wafers of the wafer set.

* * * * *